United States Patent [19]

Minagawa et al.

[11] Patent Number: 5,128,329
[45] Date of Patent: Jul. 7, 1992

[54] STABLE INSECTICIDAL PREPARATIONS IN THE FORM OF AQUEOUS EMULSION OR SUSPENSION

[75] Inventors: Fumiyasu Minagawa, Osaka; Toshiyuki Tange; Kazuyuki Maeda, both of Hyogo, all of Japan

[73] Assignees: Sumitomo Corporation, Osaka; Yuko Chemical Industries, Co., Ltd., Hyogo, both of Japan

[21] Appl. No.: 360,994

[22] Filed: Jun. 2, 1989

Related U.S. Application Data

[63] Continuation-in-part of Ser. No. 904,765, Sep. 5, 1986, abandoned, which is a continuation of Ser. No. 727,556, Apr. 26, 1985, abandoned, which is a continuation-in-part of Ser. No. 655,374, Sep. 27, 1984, abandoned, which is a continuation-in-part of Ser. No. 655,375, Sep. 27, 1984, abandoned, which is a continuation-in-part of Ser. No. 615,456, May 30, 1985, abandoned, which is a continuation-in-part of Ser. No. 615,321, May 30, 1985, abandoned.

[30] Foreign Application Priority Data

Jun. 15, 1983 [JP] Japan .................. 58-108404

[51] Int. Cl.$^5$ .............................................. A01N 57/00
[52] U.S. Cl. ........................................ 514/89; 514/113
[58] Field of Search .................................. 514/89, 113

[56] References Cited

U.S. PATENT DOCUMENTS

| 4,173,651 | 11/1979 | Muramoto | 424/306 |
| 4,303,640 | 12/1981 | Fuyama | 424/78 |
| 4,399,287 | 8/1983 | Baillie | 548/119 |
| 4,456,569 | 6/1984 | Rodson | 264/4.7 |

FOREIGN PATENT DOCUMENTS

| 1145252 | 4/1983 | Canada | 167/4.6 |
| 1177723 | 11/1984 | Canada | 167/4.1 |

OTHER PUBLICATIONS

McCutcheon's Detergents & Emulsifiers D&E 1971 Annal.

Primary Examiner—Stanley J. Friedman
Assistant Examiner—Russell Travers
Attorney, Agent, or Firm—Ladas & Parry

[57] ABSTRACT

Physically and chemically stable insecticidal preparation in the form of aqueous emulsion or suspension is provided wherein active ingredients which are oily or solid and hardly soluble or insoluble in water are mixed in water with nonionic surfactants having an HLB value of 11 or less and thickeners.

1 Claim, No Drawings

STABLE INSECTICIDAL PREPARATIONS IN THE FORM OF AQUEOUS EMULSION OR SUSPENSION

This is a continuation-in-part of Patent Application Ser. No. 904,765 filed Sep. 5, 1986 which is a continuation of Ser. No. 727,556 filed Apr. 26, 1985 which is a continuation-in-part of Ser. Nos. 655,374 and 655,375 filed Sep. 27, 1984 and Sep. 27, 1984, respectively, which are continuation-in-part of Ser. Nos. 615,456 and 615,321 filed May 30, 1985 and May 30, 1985, respectively. All are now abandoned.

The present invention relates to an improvement in an agricultural chemical preparation in the form of aqueous emulsion or suspension, said preparation containing insecticides, herbicides or fungicides.

So far as insecticidal preparations in particular, for instance, are concerned, they are usually in the form of emulsifiable concentrates, wettable powders, dusts, flowables and the like. Desired forms are chosen depending on the purposes. An aqueous preparation is preferred, because it is able to be formulated using water in place of organic solvents which often cause toxicity problems like phytotoxicity or irritation and safety problems in production, storage, transportation or application thereof.

Active ingredients used in insecticidal preparations in the form of aqueous emulsion or suspension heretofore proposed are usually hydrophobic or solid at room temperature. Any of oil-in-water emulsion formulation containing a liquid active ingredient at room temperature has not yet been put on the market, because shelf life is not long, i.e., short in stability in water. The word "stability" herein means "physical stability", i.e., separation to phases and "chemical stability", i.e., decomposition of active ingredients.

There are oil-in-water type emulsion formulations. Some of them are suspension in water containing thickeners without surfactants, or emulsion in water containing surfactants without thickeners. The former suspension is hard to keep emulsion for a long time, while the latter emulsion accompanies hydrolysis of active ingredients by surfactants during the storage until the ingredients are decomposed and they no longer work as insecticides, although there is little separation into different phases. Problems in the presence of surfactants left unsolved are short shelf life due to decomposition of active ingredient(s) and unavoidable strong irritations to eyes, nose and throat. Therefore, the active ingredients employed in such formulations must be limited to those which have high stability even when emulsified or dispersed in water by the aid of a surfactant or thickeners.

U.S. Pat. No. 4,306,640 (Fuyama et.al.) discloses that general-purpose synthetic surfactants have drawbacks in stability of the active ingredient and that oil-in-water insecticidal emulsion in issue does not employ any general purpose synthetic surfactants, but polyvinyl alcohol or gum arabic as a most suitable dispersing agent. However, polyvinyl alcohol is not surfactants ("The Merck Index, page 986, No. 7363 (1976)) and gum arabic is not general purpose synthetic surfactants but emulsifying agents only for food (Martin Glicksman, "Gum Technology in the Food Industry", p. 104 (1969)), Canadian Patent No. 1145252 discloses that nonionic surfactants except that having an aromatic ring substituted with at least one aryl radical or aralkyl radical fail to give stable emulsion. The patent does not refer to chemical stability of active ingredients, but physical stability of emulsion. U.S. Pat. No. 4,173,651 discloses an insecticidal composition in which water or aliphatic hydrocarbons having a boiling point of 150°–350° C. are used as solvents, but the patent refers to neither physical stability nor chemical stability in the case of emulsion. U.S. Pat. No. 4,399,287 discloses pesticidal and in particular herbicidal compositions in which water with a surface active agent are used, but is silent on stability.

Surfactants having HLB of-12 or more have been used in aqueous compositions of water insoluble insecticides, in order to stabilize emulsion. U.S. Pat. No. 3,948,636 discloses a flowable aqueous preparation of waterinsoluble insecticide in which surfactants employed are the ethoxylated alkylphenols, i.e., alkylaryl polyether alcohols of the general formula

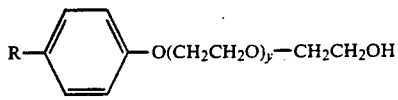

wherein $R = a\ C_8-C_{12}$ alkyl group and $y =$ an integer of 8–30. Within this class, a compound having a $C_8$-alkyl group and $y =$ an integer of 8 has the lowest HLB of 12.06. Others are as follows.

$R = C_9,\ y = 9$ HLB 13.36
$R = C_9,\ y = 15$ HLB 15.26
$R = C_{10},\ y = 9$ HLB 13.08
$R = C_{10},\ y = 15$ HLB 15.03

After the present inventors' extensive study to find a method for producing an agricultural chemical preparation of either aqueous emulsion or suspension in a simple manner, they succeeded to find the fact that any of solid or oily active ingredients which are hardly soluble or insoluble in water but soluble in or miscible with surfactants at room or elevated temperature are able to be formulated into a storage-stable aqueous preparation. In accordance therewith, insecticidal chemical preparations are obtained in which the suspensions physically stable and the active ingredient are held chemically stable for a long period of time. Furthermore the preparations are handled without any risk of inflammation in the storage or transportation thereof and markedly decreased in the toxicity to mammals.

Accordingly to the present invention, the use of nonionic surfactants having HLB value of 11 or less, preferably having HLB value of 10 or less, gives chemical stability of the ingredients as well as physical stability of the preparations for a long time of period such as two or three years. Addition of thickeners makes viscosity of the preparation suitable for spraying.

The present insecticidal preparation in the form of aqueous emulsion or suspension comprises (1) 0.5 to 60% by weight of one or more active ingredient(s),
(2) 0.3 to 50% by weight of one or more nonionic surfactant(s) having an HLB value of 11 or less,
(3) a thickener, and
(4) the balance of water.

The active ingredient is hardly soluble or insoluble in water (i.e., the solubility in water being 1% by weight or less at 20° C.). The oily ingredient means to include oily and semioily ones and is soluble in or miscible with the nonionic surfactant at room or elevated temperatures (i.e., about 20° to 50° C.). The solid ingredient is still insoluble in the nonionic surfactant even at elevated temperature. It is preferred that an amount of the solid ingredient is small when oily ingredients with solid ones are employed.

In case of a solid or powder technical material is employed, it is desirable to make it fine particles by any conventional milling equipment before mixing to prepare the suspension. The order of adding the ingredients is critical especially when a liquid technical material is employed.

Insecticides

They may be any of organophosphates, pyrethroides, carbamates or others.

(1) Organophosphate insecticides
   Cyanophos [0-(4-cyanophenyl) 0,0-dimethyl phosphorothioate]
   Diazinon [0,0-diethyl 0-2-isopropyl-6-methyl-pyrimidin4-yl phosphorothioate
   Dichlorvos [2,2-dichlorovinyl dimethylphosphate]
   Prothiophos [0-2,4-dichlorophenyl 0-ethyl-S-propyl phosphorodithioate]
   Chloropyrifos [0-3,5,6-trichloro-2-pyridyl 0,0-diethyl phosphorothioate]
   Fenitrothion [0,0-dimethyl 0-4-nitro-m-tolyl phosphorothioate]
   Fenchlorphos [0,0-dimethyl 0-2,4,5-trichlorophenyl phosphorothioate]
   Fenthion [0,0-dimethyl 0-4-methylthio-m-tolyl phosphorothioate]
   Bromophos [0-4-bromo-2,5-dichlorophenyl 0,0-dimethyl phosphorothioate]
   Malathion [S-1,2-bis(ethoxycarbonyl)ethyl 0,0-dimethyl phosphorodithioate]
   Chlorpyrifosmethyl [-0-3,5,6-trichloro-2-pyridyl 0,0-dimethyl phosphorothioate]
   Parathion [0,0-diethyl 0-4-nitrophenyl phosphorothioate]
   Sulprofos [0-ethyl 0-4-methylthiophenyl S-propyl phosphorodithioate]
   Phosalone [S-6-chloro-2,3-dihydro-2-oxobenzoxazol3-ylmethyl-0,0-diethyl phosphorodithioate]
   Acephate [0-,S-dimethyl N-acetylphosphoramidothioate]
   Pyridaphenthion [0,0-diethyl 0-(2,3-dihydro-3-oxo2-phenyl-6-pyridazinyl)-phosphorothioate]
   Temephos [0,0,0',0'-tetramethyl 0,0'-thiodip-phenylene bis(phosphorothioate)]
   Phoxim [0,0-diethyl 0-(α-cyanobenzilideneamino) thiophosphate]

(2) Pyrethroid insecticides
   Allethrin [(RS)-3-allyl-2-methyl-4-oxocyclopent2-enyl (1RS)cis, trans-chrysanthemate]
   Permethrin [3-phenoxybenzyl (1RS)cis,trans-3-(2,2-dichlorovinyl)-2,2-dimethylcyclopropanecarboxylate]
   Phenothrin [3-phenoxybenzyl (1RS)cis,transchrysanthemate]
   Tetramethrin [cyclohex-1-ene-1,2dicarboximidomethyl (1RS)cis,trans-chrysanthemate]
   Furamethrin [5-(2-propynyl)-2-furylmethyl (1RS)cis,trans-chrysanthemate]
   Resmethrin [5-benzyl-3-furylmethyl (1RS)cis, trans-chrysanthemate]
   Fenvalerate [α-cyano-3-phenoxybenzyl α-isopropyl4-chlorophenylacetate]
   Cyfluthrin [cyano-(4-fluoro-3-phenoxyphenyl)-methyl 3(2,2-dichloroethenyl)-2,2-dimethylcyclopropanecarboxylate]
   Deltamethrin [(S)-2-cyano-3-phenoxybenzyl (1R,3R)-3-(2,2-dibromovinyl)-2,2-dimethylcyclopropanecarboxylate]
   Cypermethrin [(RS)-α-cyano-3-phenoxybenzyl (1RS,3RS;1RS;3SR)-3-(2,2-dichlorovinyl)-2,2dimethylcyclopropanecarboxylate]
   Flucythrinate [(RS)-α-cyano-3-phenoxybenzyl (S)2-(4-difluoromethoxyphenyl)-3-methylbutylate]
   Cyphenothrin [α-cyano-3-phenoxybenzyl d-cis, trans-chrysanthemate]

(3) Carbamate insecticides
   Propoxur [2-isopropoxyphenyl methylcarbamate]
   Carbaryl [1-naphthyl methylcarbamate]
   BPMC [0-sec-butylphenyl methylcarbamate]
   Carbofuran [2,3-dihydro-2,2-dimethylbenzofuran7-yl methylcarbamate]
   Methomyl [S-methyl N-(methylcarbamoyloxy) thioacetimidate]

(4) Others
   Propargite [2-(4-tert-butylphenoxy)cyclohexyl prop-2-ynyl sulfite]
   Chlordane [1,2,4,5,6,7,8,8-octachloro2,3,3a,4,7,7a-hexanhyro-4,7-methanoindene]

Nonionic surfactants

Examples thereof are
(1) ethers of alkyl $C_8$–$C_{12}$ and polyoxyethylene (2–8 moles) of the formula $$\text{alkyl} - \!\!\!\bigcirc\!\!\! - O(\text{CH}_2\text{CH}_2\text{O})_n\text{H}$$

wherein alkyl is $C_8$–$C_{12}$ and n is 2–8, such as polyoxyethylene nonylphenyl ether and the like
(2) ethers of alkyl or alkenyl alcohol $C_{12}$–$C_{18}$ and polyoxyethylene (2–8 moles) of the formula $$\text{alkyl(alkenyl)} - O - (\text{CH}_2\text{CH}_2\text{O})_n - H$$

wherein alkyl(alkenyl) is $C_{12}$–$C_{18}$ and n is 2–8, such as polyoxyethylene lauryl ether and the like
(3) esters of fatty acid of $C_{12}$–$C_{18}$ and polyoxyethylene (2–8 moles), such as polyoxyethylene oleate and the like
(4) polyoxyethylene alkylamines of alkyl or alkenyl amine of $C_{12}$–$C_{18}$ and polyoxyethylene (2–6 moles), such as polyoxyethylene laurylamine and the like
(5) condensation polymer of formaldehyde (5–20 moles) and ether comprising naphthol (5–20 moles) and polyoxyethylene (4–40 moles)
(6) esters of glycerol and fatty acid ($C_{12}$–$C_{18}$), such as glycerol oleate, glycerol stearate and the like
(7) esters of pentaerythritol and fatty acid ($C_{12}$–$C_{18}$) such as pentaerythritol stearate and the like
(8) esters of sorbitan and fatty acids(s) ($C_{12}$–$C_{18}$) and polyoxyethylene (4–20 moles) sorbitan and fatty acid(s) ($C_{12}$–$C_{18}$), such as sorbitan monooleate, sorbitan stearate, sorbitan palmitate, sorbitan laurate, polyoxyethylene-sorbitan oleate and the like.

These surfactants may be used each alone or in the form of a mixture of two or more.

Thickeners

They are, for example, polyvinyl alcohol, xanthan gum, CMC, carrageenan, tragacanth gum, magnesium aluminum silicate like veegum (product of R.f. Vanderbilt Co., Inc.), Laponite (product of Laporte industries Ltd.) and gum arabic. The preferable are xanthan gum, polyvinyl alcohol, CMC, carrageenan, tragacanth gum, magnesium aluminum silicate and Laponite.

The agricultural chemical preparation of the present invention may additionally contain stabilizers such as pH regulators for the purpose of further improving the stability of active ingredients, preservatives for preventing the contamination due to microorganisms and/or agents for the depression of freezing point in order to prevent the preparation from freezing at cold area.

The stabilizers usable in the present invention include, for example, phosphates, aliphatic acid diethanolamide, butylhydroxytoluene and the like.

The preservatives usable in the present invention include, for example, PCMX, dehydroacetic acid, butyl p-hydroxybenzoate and the like.

The preparation of aqueous emulsion or suspension thus obtained in accordance with the present invention is characterized by the following advantages, as compared with a conventional emulsion or suspension preparation.

(1) Even active ingredients said to be chemically unstable are able to be stabilized as demonstrated in Tables 6, 7 and 13.

(2) Active ingredients which are liquid at room temperature are able to be formulated into the present aqueous preparation, and a mixture of a liquid active ingredient and a solid one is able to be formulated into the present aqueous preparation as shown in Examples 29 and 30.

(3) Nasal and eye irritations which have been unavoidable due to surfactants, having an HLB value higher than 11 are able to be markedly decreased as demonstrated in Table 16.

(4) Because of using a nonionic surfactant having an HLB value of 11 or less, the present preparation is superior in the spreadability onto the surfaces to be applied and residual effect against German cockroaches as shown in Table 15, and comparable in quick knockdown activity against house files, as compared with a commercially available emulsifiable concentrate.

(5) Stable spray solution is able to be easily prepared, when the preparation of the present invention is diluted into water.

The present invention will be illustrated in more detail with references to the following Examples which are only illustrative and not intended to limit the scope of the present invention. In Examples, the active ingredients used are expressed by each common name.

EXAMPLE 1

Fenitrothion (oily compound) (10 g) was mixed with sorbitan monooleate (HLB 4.3, 5 g), and the mixture was suspended in an aqueous solution of xanthan gum (0.6 g) in deionized water (84.4 g) at 25° C. to obtain an aqueous suspension preparation (100 g) of fenitrothion.

EXAMPLE 2

Example 1 was repeated, provided that fenthion (oily compound) was used in place of fenitrothion, thereby obtaining an aqueous suspension preparation of fenthion.

EXAMPLE 3

Example 1 was repeated, provided that cyanophos (oily compound) was used in place of fenitrothion, thereby obtaining an aqueous suspension preparation of cyanophos.

COMPARATIVE EXAMPLE 1

A mixture of fenitrothion (10 g) and polyoxyalkylene polystyrylphenyl ether (HLB 13, 15 g) was mixed with aqueous solution of diethyleneglycol monobutyl ether (15 g) in deionized water (60 g) to obtain an aqueous suspension preparation (100 g).

COMPARATIVE EXAMPLE 2

Comparative Example 1 was repeated, provided that fenthion was used in place of fenitrothion, thereby obtaining an aqueous suspension preparation of fenthion.

COMPARATIVE EXAMPLE 3

Comparative Example 1 was repeated, provided that cyanophos was used in place of fenitrothion, thereby obtaining an aqueous suspension preparation of cyanophos.

The compositions were stored in constant temperature baths for various periods of time, then emulsion condition of the composition and decomposition percentage of the active ingredient in the composition after the storage were checked and measured. The data are shown in table 1.

The decomposition percentage:

Concentration of active ingredients in the composition was analyzed by gaschromatograph, then the decomposition percentage was calculated by the following formula.

$$\text{decomposition percentage} = \frac{\text{conc. of } A.I.^* \text{ (before storage)} - \text{conc. of } A.I.^* \text{ (after storge)}}{\text{conc. of } A.I.^* \text{ (before storage)}} \times 100$$

*active ingredient

TABLE 1

| Example No. | | Decomposition percentage of active ingredient after storage at 40° C. for 30 days (%) |
|---|---|---|
| Example No. | 1 | 0.5 |
| | 2 | 0.2 |
| | 3 | 0.4 |
| Comparative Example No. | 1 | 38 |
| | 2 | 12 |
| | 3 | 35 |

Table 1 shows that preparations of Example No. 1–3 where a surfactant having HLB value of 4.3 was used are excellent in stability of active ingredients compared with Comparative Example Nos. 1–3 where a surfactant having HLB values of 13 was used.

EXAMPLES 4 TO 7 AND COMPARATIVE EXAMPLES 4 TO 6

In a manner similar to that of Example 1, each preparation having the composition as shown in the following table 2 was obtained.

TABLE 2

| Composition | Example No. 4 | 5 | 6 | 7 | Comparative Example No. 4 | 5 | 6 |
|---|---|---|---|---|---|---|---|
| Fenitrothion (oily compound) | 10 | 10 | 10 | 10 | 10 | 10 | 10 |
| polyoxyethylen nonylphenyl ether (HLB 5.5) | 5 | — | — | — | — | — | — |
| polyoxyethylen nonylphenyl ether (HLB 7.5) | — | 5 | — | — | — | — | — |
| polyoxyethylen nonylphenyl ether (HLB 8.9) | — | — | 5 | — | — | — | — |
| polyoxyethylen nonylphenyl ether (HLB 10.9) | — | — | — | 5 | — | — | — |
| polyoxyethylen nonylphenyl ether (HLB 13.3) | — | — | — | — | 5 | — | — |
| polyoxyethylen nonylphenyl ether (HLB 15.0) | — | — | — | — | — | 5 | — |
| polyoxyethylen nonylphenyl ether (HLB 16.0) | — | — | — | — | — | — | 5 |
| Sodium dehydroacetate | 0.2 | 0.2 | 0.2 | 0.2 | 0.2 | 0.2 | 0.2 |
| Xanthan gum | 0.6 | 0.6 | 0.6 | 0.6 | 0.6 | 0.6 | 0.6 |
| Deionized water | 84.2 | 84.2 | 84.2 | 84.2 | 84.2 | 84.2 | 84.2 |

EXAMPLE 8 TO 11 AND COMPARATIVE EXAMPLE 7 TO 9

Similarly, each preparation having the composition as shown in the following table 3 was obtained.

TABLE 3

| Composition | Example No. 8 | 9 | 10 | 11 | Comparative Example No. 7 | 8 | 9 |
|---|---|---|---|---|---|---|---|
| Fenthion (Oily compound) | 5 | 5 | 5 | 5 | 5 | 5 | 5 |
| Polyoxyethylene lauryl ether (HLB 5.5) | 5 | — | — | — | — | — | — |
| Polyoxyethylene lauryl ether (HLB 7.1) | — | 5 | — | — | — | — | — |
| Polyoxyethylene lauryl ether (HLB 8.6) | — | — | 5 | — | — | — | — |
| Polyoxyethylene lauryl ether (HLB 10.4) | — | — | — | 5 | — | — | — |
| Polyoxyethylene lauryl ether (HLB 14.1) | — | — | — | — | 5 | — | — |
| Polyoxyethylene lauryl ether (HLB 15.6) | — | — | — | — | — | 5 | — |
| Polyoxyethylene lauryl ether (HLB 18.4) | 5 | — | — | — | — | — | 5 |
| Sodium dehydroacetate | 0.2 | 0.2 | 0.2 | 0.2 | 0.2 | 0.2 | 0.2 |
| Xanthan gum | 0.6 | 0.6 | 0.6 | 0.6 | 0.6 | 0.6 | 0.6 |
| deionized water | 89.2 | 89.2 | 89.2 | 89.2 | 89.2 | 89.2 | 89.2 |

EXAMPLE 12 AND 13 AND COMPARATIVE EXAMPLE 10 TO 12

Similarly, each preparation having the composition as shown in the following table 4 was obtained.

TABLE 4

| Composition | Example No. 12 | 13 | Comparative Example No. 10 | 11 | 12 |
|---|---|---|---|---|---|
| Diazinon (oily compound) | 5 | 5 | 5 | 5 | 5 |
| Polyoxyethylen oleate (HLB 2.5) | 5 | — | — | — | — |
| Polyoxyethylen oleate (HLB 9.3) | — | 5 | — | — | — |
| Polyoxyethylen oleate (HLB 11.4) | — | — | 5 | — | — |
| Polyoxyethylen oleate (HLB 15.3) | — | — | — | 5 | — |
| Polyoxyethylen oleate (HLB 16.1) | — | — | — | — | 5 |
| Potassium phosphate | 0.1 | 0.1 | 0.1 | 0.1 | 0.1 |
| Disodium hydrogenphosphate | 1.5 | 1.5 | 1.5 | 1.5 | 1.5 |
| Xanthan gum | 0.6 | 0.6 | 0.6 | 0.6 | 0.6 |
| deionized water | 87.8 | 87.8 | 87.8 | 87.8 | 87.8 |

EXAMPLE 14 AND 16 AND COMPARATIVE EXAMPLE 13 TO 14

Similarly, each preparation having the composition as shown in the following table 5 was obtained.

TABLE 5

| Composition | Example No. 14 | 15 | 16 | Comparative Example No. 13 | 14 |
|---|---|---|---|---|---|
| Fenthion (oily compound) | 5 | 5 | 5 | 5 | 5 |
| Tetramethrin (solid compound) | 0.5 | 0.5 | 0.5 | 0.5 | 0.5 |
| Permethrin (oily compound) | 2 | 2 | 2 | 2 | 2 |
| Polyoxyethylene laurylamine (HLB 6.5) | 5 | — | — | — | — |
| Polyoxyethylene laurylamine (HLB 7.8) | — | 5 | — | — | — |
| Polyoxyethylene laurylamine (HLB 10.9) | — | — | 5 | — | — |
| Polyoxyethylene laurylamine (HLB 14.1) | — | — | — | 5 | — |
| Polyoxyethylene laurylamine (HLB 16.5) | — | — | — | — | 5 |
| Sodium dehydroacetate | 0.2 | 0.2 | 0.2 | 0.2 | 0.2 |
| Xanthan gum | 0.6 | 0.6 | 0.6 | 0.6 | 0.6 |
| deionized water | 86.7 | 86.7 | 86.7 | 86.7 | 86.7 |

Stability was listed in table 6.

TABLE 6

| | HLB** | S.C.* | P.S.** | Decomposition percentage of active ingredient after storage at 50° C. for 1 month (%) |
|---|---|---|---|---|
| Example No. 4 | 5.5 | 2 | OK | 6 |
| 5 | 7.5 | 2 | OK | 8 |
| 6 | 8.9 | 2 | OK | 9 |

TABLE 6-continued

|  |  | **HLB | *S.C. | **P.S. | Decomposition percentage of active ingredient after storage at 50° C. for 1 month (%) |
|---|---|---|---|---|---|
|  | 7 | 10.9 | 2 | OK | 12 |
| Comparative | 4 | 13.3 | 2 | OK | 28 |
| Example No. | 5 | 15.0 | 2 | OK | 43 |
|  | 6 | 16.0 | 2 | OK | 58 |
| Example No. | 8 | 5.5 | 2 | OK | 2 |
|  | 9 | 7.1 | 2 | OK | 2 |
|  | 10 | 8.6 | 2 | OK | 2 |
|  | 11 | 10.4 | 2 | OK | 3 |
| Comparative | 7 | 14.1 | 2 | OK | 8 |
| Example No. | 8 | 15.6 | 2 | OK | 11 |
|  | 9 | 18.4 | 2 | OK | 26 |
| Example No. | 12 | 2.5 | 2 | OK | 5 |
|  | 13 | 9.3 | 2 | OK | 6 |
| Comparative | 10 | 11.4 | 2 | OK | 10 |
| Example No. | 11 | 15.3 | 2 | OK | 15 |
|  | 12 | 16.1 | 2 | OK | 21 |
|  |  |  |  |  | Fenthion / Tetramethrin / Permethrin |
| Example No. | 14 | 6.5 | 2 | OK | 2 / 1 / 0.1 |
|  | 15 | 7.8 | 2 | OK | 2 / 1 / 0.1 |
|  | 16 | 10.9 | 2 | OK | 4 / 5 / 0.3 |
| Comparative | 13 | 14.1 | 2 | OK | 11 / 8 / 0.6 |
| Example No. | 14 | 16.5 | 2 | OK | 14 / 16 / 0.8 |

*Storage conditions: 1: 40° C., 30 days; 2: 50° C. one month 3: 50° C., one week
**Stability of emulsion
OK ... complete emulsion
sep ... seperated
**
**HLB value of surfactants Table 6 shows that surfactants having HLB of 11 or smaller serve to control decomposition of insecticides at the small level and to have active ingredients performed as insecticides.

EXAMPLES 17 TO 30 AND COMPARATIVE EXAMPLES 15 AND 16

Similarly, each preparation having the composition as shown in the following table 7 was obtained. Stability was also mentioned in the table.

TABLE 7

| Example No. | Composition | Amount (g) | *S.C. | **P.S. | ***C.S. |
|---|---|---|---|---|---|
| 17 | Fenitrothion | 10 |  |  | 1.0 |
|  | Sorbitan monolaurate (HLB 8.1) | 5 | 3 | OK |  |
|  | Xanthan gum | 0.6 |  |  |  |
|  | deionized water | 84.4 |  |  |  |
| 18 | Fenthion | 10 |  |  | 1.0 |
|  | Sorbitan monooleate (HLB 4.3) | 5 | 2 | OK |  |
|  | Xanthan gum | 0.6 |  |  |  |
|  | Sodium dehydroacetate | 0.2 |  |  |  |
|  | deionized water | 84.2 |  |  |  |
| 19 | Propargite | 30 |  |  | 0.2 |
|  | Sorbitan monooleate (HLB 4.3) | 5 |  |  |  |
|  | Polyvinyl alcohol[a] | 7 | 3 | OK |  |
|  | Potassium phosphate | 0.1 |  |  |  |
|  | Disodium hydrogenphosphate | 1.5 |  |  |  |
|  | Sodium dehydroacetate | 0.2 |  |  |  |
|  | Deionized water | 56.2 |  |  |  |
| 20 | Propargite | 40 |  |  | 0.2 |
|  | Sorbitan monooleate (HLB 4.3) | 5 |  |  |  |
|  | Polyvinyl alcohol[a] | 5 | 3 | OK |  |
|  | Potassium phosphate | 0.1 |  |  |  |
|  | Disodium hydrogenphosphate | 1.5 |  |  |  |
|  | Sodium dehydroacetate | 0.2 |  |  |  |
|  | deionized water | 48.2 |  |  |  |
| 21 | Chlordan | 60 |  |  | 0 |

TABLE 7-continued

| Example No. | Composition | Amount (g) | *S.C. | **P.S. | ***C.S. |
|---|---|---|---|---|---|
|  | Sorbitan monooleate (HLB 4.3) | 5 | 2 | OK |  |
|  | Polyvinyl alcohol[a] | 3.5 |  |  |  |
|  | deionized water | 31.5 |  |  |  |
| 22 | Cyanophos | 10 |  |  | 0.5 |
|  | Polyoxyethylene nonylphenyl ether (HLB 5.5) | 5 | 3 | OK |  |
|  | Xanthan gum | 0.6 |  |  |  |
|  | deionized water | 84.4 |  |  |  |
| 23 | Diazinon | 30 |  |  | 1.0 |
|  | Polyoxyethylene oleate (HLB 9.3) | 5 |  |  |  |
|  | Polyvinyl alcohol[a] | 7 | 3 | OK |  |
|  | Potassium phosphate | 0.1 |  |  |  |
|  | Disodium hydrogenphosphate | 1.5 |  |  |  |
|  | Sodium dehydroacetate | 0.2 |  |  |  |
|  | deionized water | 56.2 |  |  |  |
| 24 | Fenthion | 40 |  |  | 0.5 |
|  | Polyoxyethylene lauryl ether (HLB 8.6) | 5 | 3 | OK |  |
|  | Polyvinyl alcohol[a] | 5 |  |  |  |
|  | deionized water | 50 |  |  |  |
| 25 | Fenitrothion | 10 |  |  | 1.0 |
|  | Permethrin | 2 |  |  | 0.1 |
|  | Tetramethrin | 1 | 3 | OK | 0.5 |
|  | Sorbitan monooleate (HLB 4.3) | 5 |  |  |  |
|  | Xanthan gum | 0.6 |  |  |  |
|  | Sodium dehydroacetate | 0.2 |  |  |  |
|  | deionized water | 81.2 |  |  |  |
| 26 | Fenitrothion | 5 |  |  | 2 |
|  | Tetramethrin | 0.5 |  |  | 5 |
|  | Sorbitan monooleate (HLB 4.3) | 10 | 2 | OK |  |
|  | Xanthan gum | 0.6 |  |  |  |
|  | Sodium dehydroacetate | 0.2 |  |  |  |
|  | deionized water | 83.7 |  |  |  |
| 27 | Fenitrothion | 10 |  |  | 0.7 |
|  | Tetramethrin | 1 |  |  | 0.7 |
|  | Sorbitan monooleate (HLB 4.3) | 5 | 3 | OK |  |
|  | Xanthan gum | 0.6 |  |  |  |

TABLE 7-continued

| Example No. | Composition | Amount (g) | * S.C. | ** P.S. | *** C.S. |
|---|---|---|---|---|---|
| | Sodium dehydroacetate | 0.2 | | | |
| | deionized water | 83.2 | | | |
| 28 | Diazinon | 40 | | | |
| | Sorbitan monolaurate (HLB 8.1) | 3 | | | |
| | Polyoxyethylene laurylamine | 2 | | | |
| | Polyvinyl alcohol[a] | 5 | 3 | OK | 0.7 |
| | Potassium phosphate | 0.1 | | | |
| | Disodium hydrogenphosphate | 1.5 | | | |
| | Sodium dehydroacetate | 0.2 | | | |
| | deionized water | 48.2 | | | |
| 29 | Permethrin | 15 | | | 0.1 |
| | Thiabendazole | 5 | | | |
| | Sorbitan monooleate (HLB 4.3) | 10 | 3 | OK | |
| | Polyvinyl alcohol[a] | 3.3 | | | |
| | deionized water | 66.7 | | | |
| 30 | Fenitrothion | 15 | | | 0.9 |
| | AMICAL 48 | 5 | 3 | OK | |
| | Sorbitan monooleate (HLB 4.3) | 10 | | | |
| | Polyvinyl alcohol[a] | 3.3 | | | |
| | deionized water | 66.7 | | | |
| Comparative Example | | | | | |
| 15 | Tetramethrin | 5 | | | 12 |
| | Polyoxyethyelene nonylphenyl ether (HLB 16.0) | 5 | 1 | OK | |
| | Sodium dehydroacetate | 0.2 | | | |
| | Xanthan gum | 0.6 | | | |
| | deionized water | 89.2 | | | |
| 16 | Fenitrothion | 10 | | | 42 |
| | Tetramethrin | 1 | | | 14 |
| | Polyoxyethylene nonylphenyl ether (HLB 16.0) | 5 | 1 | OK | |
| | Sodium dehydroacetate | 0.2 | | | |
| | Xanthan gum | 0.6 | | | |
| | deionized water | 83.2 | | | |

*Storage conditions
1: 40° C., 30 days; 2: 50° C., one month; 3: 50° C., one week
**Stability of emulsion
OK ... complete emulsion
sep ... separated
***Decomposition percentate of active ingredient (%)
[a]Polyvinyl alcohol having the polymerization degree of 1000 or less and the saponification degree of 86.5 to 89.0 mole %.

EXAMPLE 31

Fenitrothion (10 g) was mixed with sorbitan monolaurate (10 g) (HLB 8.1), and the resulting mixture was mixed with a 0.6% by weight aqueous solution of xanthan gum (80 g) to obtain an aqueous emulsion preparation of fenitrothion (100 g) having an effective ingredient content of 10% by weight.

EXAMPLE 32

A mixture of phenothrin (50 g) and polyoxyethylenesorbitan trioleate (20 g) (HBL 11) was mixed with a 0.5% by weight aqueous solution of xanthan gum (30 g) to obtain an aqueous emulsion preparation of phenothrin (100 g) having an effective ingredient content of 50% by weight. After the composition was stored at 50° C. for one week, no physical change in emulsion was observed and decomposition percentage of phenothrin was 0.2.

EXAMPLE 33

A mixture of fenitrothion (5 g) and tetramethrin (0.5 g) was mixed with sorbitan monolaurate (HLB 8.1) (10 g) at about 60° C., and the resulting mixture was mixed with a 0.6% by weight aqueous solution of xanthan gum (84.5 g) to obtain a mixed aqueous emulsion preparation of fenitrothion and tetramethrin (100 g) having each effective ingredient content of 5% by weight and 0.5% by weight, respectively. After the composition was stored at 50° C. for one week, no physical change in emulsion was observed and decomposition percentages of fenitrothion and tetramethrin were 1.8 and 0.5, respectively.

EXAMPLE 34

A mixture of phenothrin (5 g), tetramethrin (0.5 g) and permethrin (1 g) was mixed with a mixture of sorbitan monolaurate (5 g) (HLB 8.1), sorbitan monopalmitate (HLB 6.9) (1 g) and polyoxyethylenesorbitan trioleate (HLB 11) (1 g), and the resulting mixture was mixed with 0.6% by weight aqueous solution of xanthan gum (86.5 g) to obtain a mixed aqueous emulsion preparation of phenothrin, tetramethrin and permethrin having each effective ingredient content of 5% by weight, 0.5% by weight and 1% by weight, respectively.

After the composition was stored at 50° C. for one week, no physical change in the emulsion was observed and decomposition percentages of phenothrin, tetramethrin and permethrin were 0.2, 0.8 and 0.1, respectively.

EXAMPLES 35 TO 38

TABLE 8

| | Composition | (w/w %) | | | |
|---|---|---|---|---|---|
| | | 35 | 36 | 37 | 38 |
| Active ingredient | Fenitrothion | 10 | — | — | — |
| | Fenthion | — | 5 | — | — |
| | Daizinon | — | — | 5 | — |
| | Cyanophos | — | — | — | 5 |
| | Tetramethrin | — | — | 0.5 | — |
| Polyhydric alcohol type nonionic surfactant | Sorbitan monooleate (HLB 4.3) | 5 | — | 5 | 5 |
| | Glycerol monostearate (HLB 3.5) | — | 5 | — | — |
| Thickener | Xanthan gum | 0.6 | — | 0.6 | 0.6 |
| | Polyvinyl alcohol | — | 5 | — | — |
| Preservative | Sodium dehydroacetate | 0.2 | 0.2 | 0.5 | 0.2 |
| Stabilizer | 1/15M Sorensen's buffer solution (pH 7.73) | — | — | Balance | — |
| Diluent | Water purified according to the Japanese pharmacopoeia | Balance | Balance | — | Balance |
| Storage conditions | | 50° C. one week | | | |
| P.S.** | | OK | OK | OK | OK |
| C.S.*** | | 0.5 | 0.5 | Dai. 1.0 Tet. 1.0 | 0.4 |

**Stability of emulsion
OK ... complete emulsion
sep ... separated
***Decomposition percentage of active ingredient

EXAMPLES 39 TO 40

TABLE 9

| Composition | | 39 (w/w %) | 40 (w/w %) |
|---|---|---|---|
| Active ingredient | Pyridaphenthion | 10 | — |
| | Prothiofos | — | 10 |
| Polyhydric alcohol type nonionic surfactant | Sorbitan monopalmitate (HLB 6.9) | 5 | — |
| | Sorbitan monolaurate (HBL 8.1) | — | 5 |
| Thickener | Xanthan gum | 0.6 | 0.4 |
| | Guar gum | — | 0.2 |
| Preservative | Sodium dehydroacetate | 0.2 | — |
| | Lactic acid | — | 0.4 |
| Diluent | Water purified according to the Japanese pharmacopoeia | Balance | Balance |
| Storage condition | | 50° C., one week | |
| P.S.** | | OK | OK |
| C.S.*** | | 0.5 | 2.0 |

**Stability of emulsion
OK ... complete emulsion
sep ... separated
***Decomposition percentage of active ingredient

EXAMPLES 41 TO 46

TABLE 10

| Composition | | 41 | 42 | 43 | 44 | 45 | 46 |
|---|---|---|---|---|---|---|---|
| Active ingredient | Temephos | 10 | — | — | — | — | — |
| | Resmethrin | — | — | 3 | — | — | — |
| | Permethrin | — | 20 | — | 4 | — | — |
| | Fenitrothion | — | — | — | 5 | — | 10 |
| | Tetramethrin | — | — | — | 1 | .5 | 1 |
| Polyhydric alcohol type nonionic surfactant | Sorbitan monooleate (HLB 4.3) | 5 | — | — | 5 | — | — |
| | Polyoxyethylene-nonylphenyl ether (HLB 5.5) | — | — | — | — | 5 | 5 |
| | Polyoxyethylene-sorbitan trioleate (HLB 11) | — | 50 | 10 | — | — | — |
| Thickener | Xanthan gum | — | 0.02 | 0.2 | 0.6 | 0.6 | 0.6 |
| | Polyvinyl alcohol | 5 | — | — | — | — | — |
| | Tragacanth gum | 0.2 | — | — | — | — | — |
| Preservative | Sodium dehydroacetate | 0.2 | — | — | 0.2 | 0.2 | 0.2 |
| | Sorbic acid | — | 0.1 | — | — | — | — |
| | Lactic acid | — | — | 2 | — | — | — |
| Diluent | Water purified according to the Japanese pharmacopoeia | Balance | Balance | Balance | Balance | Balance | Balance |
| Colorant | Blue No. 1 | — | — | — | 0.001 | — | — |
| Storage conditions | | 50° C., one week | | | | 40° C., 30 days | |
| P.S.** | | OK | OK | OK | OK | OK | OK |
| C.S.*** | | 1.5 | 0.2 | 0.8 | Per. 0.1 Fen. 1.2 Tet. 1.0 | 2 | Fen. 5 Tet. 3 |

**Stability of emulsion
OK ... complete emulsion
sep ... separated
***Decomposition percentage of active ingredient

EXAMPLES 47 TO 50

TABLE 11

| Example No. | Composition | Amount (g) | * S.C. | ** P.S. | *** C.S. |
|---|---|---|---|---|---|
| 47 | Phoxim | 12 | | | 1.2 |
| | Sorbitan monooleate (HLB 4.3) | 5 | 3 | OK | |
| | Polyvinyl alcohol$^{a)}$ | 8 | | | |
| | deionized water | 75 | | | |
| 48 | Chlorpyrifos | 5 | | | 0.5 |
| | Polyoxyethylene nonylphenyl ether (HLB 10.9) | 10 | 3 | OK | |
| | Polyvinyl alcohol$^{a)}$ | 8 | | | |
| | deionized water | 77 | | | |
| 49 | Fenchlorofos | 5 | | | 2.0 |
| | Sorbitan monooleate (HLB 4.3) | 5 | 3 | OK | |
| | Polyvinyl alcohol$^{a)}$ | 9 | | | |
| | deionized water | 81 | | | |
| 50 | Malathion | 10 | | | 1.0 |
| | Sorbitan monooleate (HLB 4.3) | 5 | 3 | OK | |
| | Xanthan gum | 0.6 | | | |
| | deionized water | 84.4 | | | |

*Storage conditions
1: 40° C., 30 days; 2: 50° C., one month; 3: 50° C., one week
**Stability of emulsion
OK ... complete emulsion
sep ... separated
***Decomposition percentage of active ingredient (%)

$^{a)}$Polymerization degree of 1000 or less, saponification degree of 86.5 to 89.0 mol %.

EXAMPLES 51 TO 55

TABLE 12

| Example No. | Composition | Amount (g) | * S.C. | ** P.S. | *** C.S. |
|---|---|---|---|---|---|
| 51 | Allethrin | 5 | | | 0.2 |
| | Polyoxyethylene Sorbitan trioleate (HLB 11) | 5 | 3 | OK | |
| | Polyvinyl alcohol$^{a)}$ | 9 | | | |
| | deionized water | 81 | | | |
| 52 | Rethmethrin | 5 | | | 0.4 |
| | Sorbitan monooleate (HLB 8.1) | 5 | 3 | OK | |
| | Polyvinyl alcohol$^{a)}$ | 9 | | | |
| | deionized water | 81 | | | |
| 53 | Cyphenothrin | 10 | | | 0.1 |
| | Sorbitan monooleate (HLB 8.1) | 5 | 3 | OK | |
| | Polyvinyl alcohol$^{a)}$ | 8 | | | |
| | deionized water | 77 | | | |
| 54 | Flucythrinate | 1 | | | 0.1 |
| | Sorbitan monooleate (HLB 8.1) | 5 | 3 | OK | |
| | Polyvinyl alcohol$^{a)}$ | 9 | | | |
| | deionized water | 85 | | | |
| 55 | BPMC | 2 | | | 1.5 |
| | Polyoxyethylene nonylphenyl ether | 5 | 3 | OK | |
| | Polyvinyl alcohol$^{a)}$ | 9 | | | |
| | deionized water | 84 | | | |

*Storage conditions
1: 40° C., 30 days; 2: 50° C., one month; 3: 50° C., one week
**Stability of emulsion
OK . . . complete emulsion
sep . . . separated
***Decomposition percentage of active ingredient (%)
$^{a)}$Polymerization degree of 1000 or less, saponification degree of 86.5 to 89.0 mol %.

EXAMPLE 56

| Composition | Amount (g) |
|---|---|
| Fenthion | 10 |
| Polyoxyethylene arylphenyl ether condensation polymer of formaldehyde (HLB 10) | 5 |
| Polyvinyl alcohol* | 8.5 |
| deionized water | 76.5 |

Stability (50° C., 10 days)
Dispersion: No change
Decomposition of Fenthion 1.5%
*The same as that in Table 11.

TABLE 13

| | | Preparation | |
|---|---|---|---|
| | | Aqueous emulsion preparation of the present invention | Conventional solubilized oil-in-water preparation (anionic surfactant) |
| Content of active ingredient | | Fenitrothion 10% by weight | Fenitrothion 10% by weight |
| Decomposition | 1 Month | 0 | 37.5 |
| percentage (%) | 3 Months | 0.4 | 53.9 |
| (Stored at 40° C.) | 6 Months | 0.6 | not calculable |

Table 13 shows that fenitrothion which is unstable in the conventional solubilized oil-in-water preparation is able to be stabilized, in accordance with the present invention.

Insecticidal activity test

The preparation of aqueous suspension obtained in Example 26 is compared in knocking activity and residual effects respectively with the conventional emulsifiable concentrate obtained in Comparative Example 17 whose composition is:

| | |
|---|---|
| Fenitrothion | 5 |
| Tetramethrin | 0.5 |
| Calcium alkylbenzenesulfonate (anionic surfactant) | 2.3 |
| Polyoxyalkylene($C_{2-3}$, n = 5–10) alkyl ($C_{12-15}$)ether | 2.2 |
| Polyoxyethylene(n = 5–10)octylphenyl ehter | 0.5 |
| Xylene | 20 |
| Kerosene | 69.5 |

(1) Insecticidal effect against adult house flies by a filter paper contacting method Adult flies were released onto a treated filter paper with each preparation immediately after treatment

| dosage | 50 ml/m$^2$ |
|---|---|
| dilution | 10 folds |

TABLE 14

| | (%) at indicated minutes after treatment | | | | | | | | | |
|---|---|---|---|---|---|---|---|---|---|---|
| | Knock down ratio (%) | | | | | | | | KT$_{50}$ (minute second) | Mortality (%) After 24 hours |
| Preparations tested | 3 | 5 | 7 | 10 | 15 (min.) | 25 | 35 | 60 | | |
| Aqueous suspension of the present invention (Example 26) | 0 | 13.3 | 43.3 | 80.0 | 93.3 | 100 | 100 | 100 | 7' 37" | 100 |
| Conventional emulsifiable concentrate (Comparative Example 17) | 0 | 16.7 | 46.7 | 76.7 | 96.7 | 100 | 100 | 100 | 7' 14" | 100 |

The preparation of aqueous suspension in accordance with the present invention shows quick knock down activity similar to that of the conventional emulsifiabler concentrate.

(2) Insecticidal effect against German cockroaches by a glass plate contacting method Cockroaches are released onto a glass plate treated with solution of each preparation at indicated days and mortality was counted.
dilution : 10 folds
dosage : (50 ml/m$^2$)

TABLE 15

| Preparations tested | Days after treatment | Continuous contacting at the same surfaces Mortality (%) | |
|---|---|---|---|
| | | After 24 hours | After 48 hours |
| Aqueous emulsion of the present invention (Example 26) | Immediately after | 100 | — |
| | After 1 week | 100 | — |
| | After 2 weeks | 100 | — |
| | After 3 weeks | 100 | — |
| | After 4 weeks | 96.7 | 100 |
| Conventional emulsifiable concentrate (Comparative Example 17) | Immediately after | 100 | — |
| | After 1 week | 100 | — |
| | After 2 weeks | 86.7 | 100 |
| | After 3 weeks | 73.3 | 100 |
| | After 4 weeks | 50.0 | 86.7 |

10-fold diluent (50 ml/m²)

As is clear from the above results, the preparation of aqueous emulsion in accordance with the present invention is superior in the residual effect against German cockroaches to that of the conventional emulsifiable concentrate

Toxicity

TABLE 16

| | | Preparations | | | |
|---|---|---|---|---|---|
| | | 10% Aqueous emulsion of fenitrothion in accordance with the present invention (Example 1) | | Commercially available 10% emulsifiable concentrate of fenitrothion (Comparative Example 18*) | |
| Test items | | ♂ | ♀ | ♂ | ♀ |
| 1 | Acute oral toxicity test | $LD_{50}$ (ml/kg) | | | |
| | Mice | >20.0 | 15.0 | 7.1 | 9.8 |
| | Rats | 4.5 | 5.4 | 3.4 | 4.0 |
| 2 | Acute dermal toxicity test | $LD_{50}$ (ml/kg) | | | |
| | Mice | >10.0 | >10.0 | >10.0 | >10.0 |
| | Rats | >10.0 | >10.0 | >10.0 | >10.0 |
| 3 | Eye irritation test Rabbits | Original liquid shows no irritation (negative) | | Original liquid shows irritation to a slight or medium degree | |
| 4 | Skin irritation test Rabbits | Original liquid shows no irritation (negative) | | Original liquid show irritation to an extremely slight degree | |

*
| | |
|---|---|
| Fenitrothion | 10 |
| Calcium alkylbenzenesulfonate (anionic surfactant) | 2.3 |
| Polyoxyalkylene($C_{2-3}$, n = 5-10) alkyl ($C_{12-15}$)ether | 2.2 |
| Polyoxyethylene(n = 5-10)octylphenyl ether | 0.5 |
| Xylene | 20 |
| Kerosene | 65 |

The preparation according to examples 35 shows the same toxicity as that of Example 1.

We claim:

1. A stable, water based insecticidal preparation in the form of an aqueous emulsion or suspension which comprises
(1) 0.5-60% by weight of fenitrothion
(2) 0.3-50% by weight of sorbitan monooleate
(3) 0.02-7% by weight of xanthan gum
(4) the balance of water.

* * * * *